United States Patent [19]

Molin et al.

[11] Patent Number: 5,522,860
[45] Date of Patent: Jun. 4, 1996

[54] CONTROL OF AN ACTIVE IMPLANTABLE MEDICAL DEVICE

[75] Inventors: Renzo D. Molin, Bagneux; Catherine Paris, Montrouge, both of France

[73] Assignee: ELA Medical S.A., Montrouge, France

[21] Appl. No.: 363,748

[22] Filed: Dec. 23, 1994

[30] Foreign Application Priority Data

Dec. 31, 1993 [FR] France .................. 93 15960

[51] Int. Cl.⁶ .................. A61N 1/36; A61B 5/02
[52] U.S. Cl. .................. 607/20; 128/632; 607/9; 607/17
[58] Field of Search .................. 607/9, 10, 11, 607/12, 13–17, 20; 128/708, 630, 632, 635, 731; 604/66

[56] References Cited

U.S. PATENT DOCUMENTS

| | | | |
|---|---|---|---|
| 3,593,718 | 7/1971 | Kramer et al. | 128/419 P |
| 3,985,142 | 10/1976 | Wickham | 607/9 |
| 4,533,346 | 8/1985 | Coscrove, Jr. et al. | 604/66 |
| 4,596,251 | 6/1986 | Plicchi et al. | 128/419 PG |
| 4,702,253 | 10/1987 | Nappholz et al. | 128/419 PG |
| 4,779,617 | 10/1988 | Whigham | 607/9 |
| 5,050,599 | 9/1991 | Hoegnelid | 607/17 |
| 5,188,177 | 2/1993 | Steinhaus et al. | 128/708 |
| 5,249,572 | 10/1993 | Bonnet | 607/20 |
| 5,303,702 | 4/1994 | Bonnet et al. | 607/20 |
| 5,350,412 | 9/1994 | Hoegnelid et al. | 607/16 |

FOREIGN PATENT DOCUMENTS

| | | | |
|---|---|---|---|
| 011932 | 11/1979 | European Pat. Off. | A61N 1/36 |
| 151689A3 | 10/1984 | European Pat. Off. | A61N 1/36 |
| 429025A2 | 11/1990 | European Pat. Off. | A61N 1/08 |
| 576114A2 | 1/1993 | European Pat. Off. | A61N 1/365 |
| 555988A2 | 2/1993 | European Pat. Off. | A61N 1/365 |

Primary Examiner—Angela D. Sykes
Assistant Examiner—Stephen Huang
Attorney, Agent, or Firm—Orrick Herrington & Sutcliffe

[57] ABSTRACT

Process of control of an implantable active medical device. The device is under the responsive control of (enslavement to) a sensed physiological parameter. A representative magnitude of the physiological parameter is measured in the presence of a useful signal to determine a value of the parameter. Then, in the absence of the useful signal, another measure is made to determine the noise. The noise is compared to a threshold corresponding to an unacceptable level of noise. In case of crossing the noise threshold, this crossing is taken in account by a control device with a view to possible suspension of a function of the device if there is too much noise.

45 Claims, 3 Drawing Sheets

CONTROL OF AN ACTIVE IMPLANTABLE MEDICAL DEVICE

The invention concerns a control process of an implantable active medical device, more particularly for a device of the type that is functionally responsive to a sensed physiological parameter such as minute ventilation.

FIELD OF THE INVENTION

The family of implantable active medical devices includes, for example, and without limitation, cardiac pacemakers and cardiac defibrillators.

An implantable active medical device can be perturbed by the presence of electromagnetic waves emanating from various sources, such as, for example, radio-telephones, anti-theft devices or televisions. In the case of a rate responsive pacemaker, in which the delivered stimulation frequency is functionally related to a measure of a physiological parameter, the perturbing electromagnetic waves can be perceived by the physiological parameter sensor as variations of the physiological parameter. As a result, the stimulation frequency may be accelerated without valid reason. This is a particular problem for physiological sensors that depend on processing sensed electrical signals, such as occur in devices that sense minute ventilation, respiration rate, QT interval, etc.

SUMMARY OF THE INVENTION

An object of the present invention is to provide an apparatus and a process of controlling an implantable active medical device that makes a count of noise events occurring due to parasitic electromagnetic signals, so as to allow the implantable active medical device to decide whether to operate in accordance with a defined function of the sensed physiological parameter, or to suspend operation according to the function when the noise exceeds a preselected (or programmable) threshold.

Broadly, the invention concerns a control process for an implantable active medical device that has an operating mode responsive to a sensed physiological parameter, which device is of the type including an electronic circuit that senses a physiological parameter and provides an output signal representative of the magnitude of the sensed physiological parameter, and a control device that controls whether or not the implantable active device operates as a function of (i.e., in response to) the output signal. One such process includes:

a) measuring the magnitude of the output signal to determine a value of the noise;

b) comparing the value of the noise to a threshold; and, c) when the value of the noise exceeds the threshold, indicating an unacceptable level of noise exists, taking this threshold crossing into account by the control device, in view of a possible suspension of operation as a function of the output signal.

In one embodiment of the present invention, the implantable active medical device includes cardiac stimulation, and the function of the output signal for the implantable device is the adjustment of a cardiac stimulation frequency as a function of the physiological parameter. One example of a suitable physiological parameter is the minute ventilation, in which case the representative magnitude is the voltage sensed between a sensing electrode and the case (reference electrode) of the medical device, e.g., a pacemaker. More particularly, the voltage is preferably first measured during an injection of current to determine the dynamic pulmonary impedance, and then measured in the absence of current injection to determine the noise. The voltage corresponding to the noise is then compared to a threshold value. When the voltage corresponding to the noise exceeds the threshold value, this crossing is taken in account by the control device, in view of a possible suspension of the rate responsive pacing function.

In one embodiment, if the noise value is considered too high or if too much noise at an unacceptable level has occurred, e.g., during a defined time period, then the acquired pulmonary impedance last acquired (or acquired during the time interval) may be disregarded as unreliable. In such case, the stimulation frequency is provided according to a different function which is not affected by such noise.

The dynamic pulmonary impedance is defined by difference between the measured pulmonary impedance and a reference or "static" pulmonary impedance, which is obtained by integrating preceding measures of the dynamic pulmonary impedance. Methods and circuits for calculating minute ventilation and selecting a pacing frequency as a function of sensed minute ventilation are known. See, e.g., U.S. Pat. Nos. 5,249,572 and 5,303,702, which are commonly assigned and incorporated herein by reference in their entireties. See also, e.g., U.S. Pat. Nos. 4,702,253, 4,596,251, and 3,593,718.

In one implementation of the invention, the voltage can be measured during an injection of current to determine the dynamic pulmonary impedance, and the voltage can be measured outside of a current injection to determine the noise, using the same electronic sensing circuit and electrodes.

The step of taking into account a crossing of the threshold value preferably is implemented by incrementing a counter. In this case, the counter and the control device cooperate to suspend operation according to the function when the counter reaches a predetermined total. The predetermined total may be an absolute value, or it may be a total for a given period of time. In one embodiment, the counter is reset to zero if no noise (or an insufficient number of noise events) is encountered in a given time period or if the count does not exceed the threshold during that time period. Alternatively, the counter may be decremented, rather than reset.

The invention also is directed to an implantable active medical device of the type comprising an electronic circuit for sensing a physiological parameter and producing an output signal representative of the magnitude of the sensed physiological parameter, and a device to insure a function of the implantable active medical device, wherein the electronic circuit comprises a feedback amplifier system comprising a digital-to-analog converter which returns to the input of the feedback amplifier a reference signal corresponding to an average of the preceding measures of the amplifier output. Preferably, the physiological parameter sensed is the minute ventilation, and the function is the provision of the cardiac stimulation frequency as a function of the measurement of minute ventilation. More specifically, the function is responsive to a dynamic pulmonary impedance and the analog signal feedback signal is the static pulmonary impedance.

BRIEF DESCRIPTION OF THE DRAWINGS

Further features and advantages of the present invention will become more apparent from the accompanying draw

DETAILED DESCRIPTION OF THE INVENTION

Figure 1:
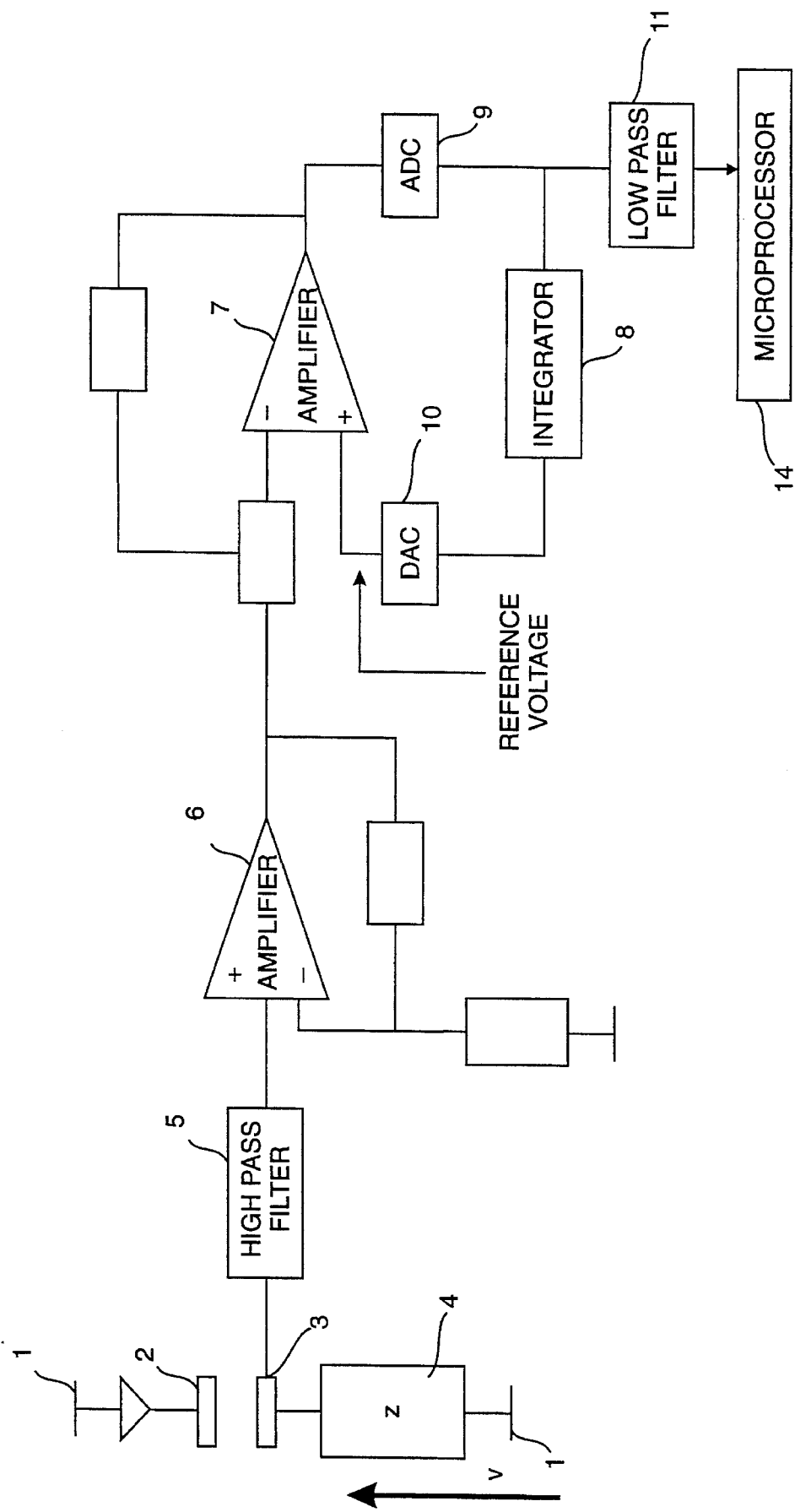
- FIG. 1 is a schematic diagram of an electronic circuit for measuring the dynamic pulmonary impedance in accordance with a preferred embodiment of the invention, in a cardiac pacemaker in which the stimulation frequency is controlled responsive to a physiological parameter that, in this example, is the minute ventilation.

Referring to FIG. 1, the implantable active medical device is illustrated as an implanted cardiac pacemaker including a case (reference electrode) 1, a current injection electrode 2, for example, at an endocardial lead tip electrode, and the sensing electrode 3, for example, an endocardial lead ring electrode. The injection of current is insured at electrode 2. The pulmonary impedance Z also is symbolized as impedance 4 between the sensing electrode 3 and the case 1. The voltage V is measured between the case 1 and the sensing electrode 3, and allows determination of the value Z of the pulmonary impedance 4 variations, thus translating the respiratory volume into sensed variations of impedance.

The electronic circuit measuring the pulmonary impedance includes a high-pass filter 5, an amplifier 6, an amplifier 7 with a feedback input comprising an integrator 8 placed between an analog-to-digital converter ("ADC") 9 and a digital-to-analog converter ("DAC") 10, and a low-pass filter 11, whose output signal (a digital code) is read by a microprocessor 14. Such sensing circuits are commercially available in the model CHORUS RM 7034 rate-responsive cardiac stimulator, which is available from ELA Medical S.A., Montrouge, France.

The functioning of the circuit is as follows. A current is injected at injection electrode 2. The voltage which is linked to the pulmonary impedance Z is measured between the other (sensing) electrode 3 and the case 1. The current injection and voltage sensing electrodes 2 and 3 can be located in the atrium or in the ventricle.

The sensed voltage is high-passed filtered at filter 5 and amplified by amplifier 6. The obtained voltage is then decreased by a reference voltage corresponding to the static pulmonary impedance, determined by a numerical integration of obtained voltage samples over the preceding voltage sampling cycles. More specifically, the sampled voltage and the static voltage inputs are differentially amplified by amplifier 7. The consequent voltage at the output of the amplifier 7 corresponds then to the dynamic pulmonary impedance. The output of amplifier 7 is digitally sampled by ADC 9. An integration by integrator 8 of the voltage in the digital form provided by ADC 9 allows the determination of the static impedance also in the form of the digital code output by integrator 8. The DAC 10 converts this digital code to an analog signal corresponding to the static impedance determined by integrator 8, which analog signal is input to the reference input of amplifier 7. The integrator 8 is preferably of the inverter type, which suppresses the input signal low frequency component (F≦0.05 Hz) and presents, according to the amplification of the signal, time-constants of increasing rapid values so as to allow the circuit to follow most closely near to the signal. This is particularly necessary in case of important (large) variations in the static impedance.

After the analog-to-digital conversion by ADC 9, the digital voltage also is filtered by low-pass filter 11, and the consequent digital code is read by the microprocessor 14. Microprocessor 14 implements the function responsive to the physiological parameter, namely an algorithm that selects the stimulation frequency as a function of the read digital code (the sensed physiological parameter) or an average of recent read digital codes. Thus, at each injection of current the microprocessor 14 executes a complete measuring cycle with injection enabling the "enslavement" function, i.e., sensing the physiological parameter minute ventilation and adjusting a stimulation frequency as a function of the sensed minute ventilation.

In accordance with the present invention, a noise measure also is obtained. In this regard, outside of a current injection, the voltage measured between the sensing electrode 2 and the case 1 corresponds to the noise sensed at electrode 2. This noise perturbs, i.e., interferes with, the pulmonary impedance during a current injection, and hence perturbs the enslavement of the pacemaker to minute ventilation, in this example.

Figure 2:
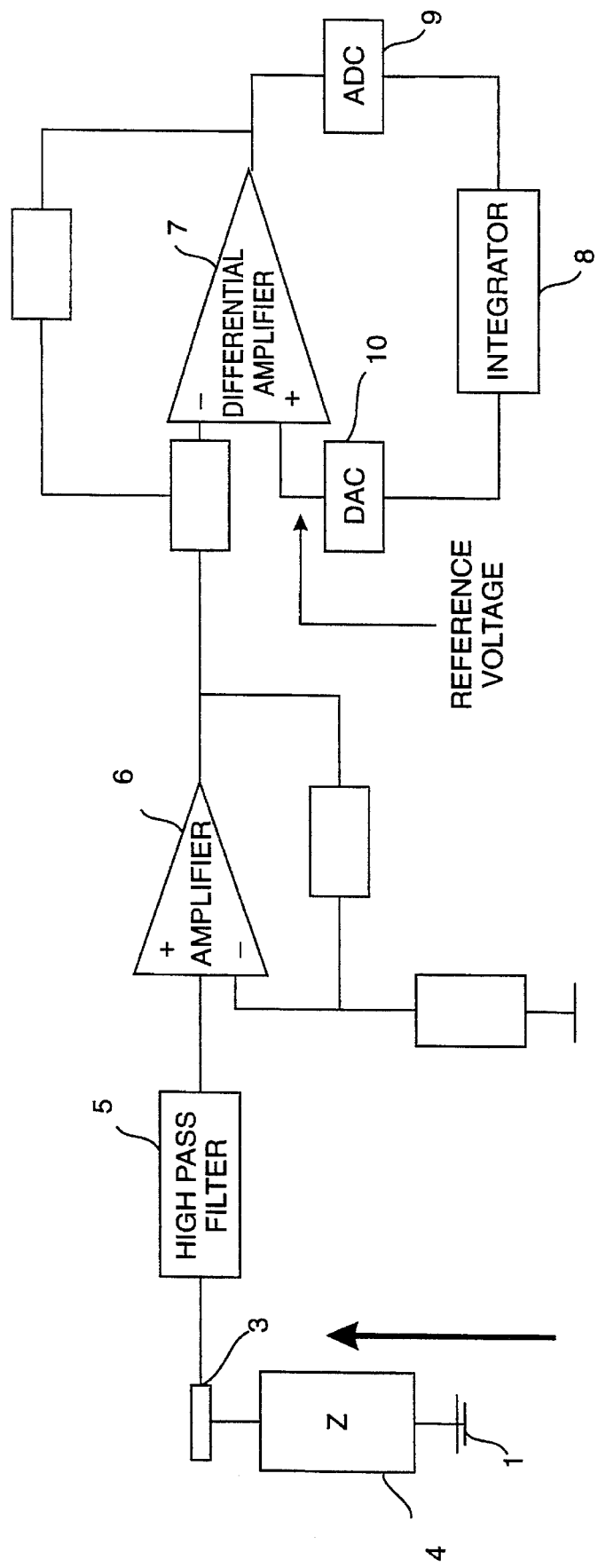
FIG. 2 is a schematic diagram of an electronic circuit for measuring the noise according to a preferred embodiment of the invention.

Referring now to FIG. 2, according to the present invention, a measure of the noise is thus undertaken by using the electronic circuit for measuring the pulmonary impedance (FIG. 1), as in the condition of measuring of the pulmonary impedance, but without any injection of current. The signal processed by the circuit illustrated in FIG. 2 is the signal present on the electrode 3 during a sampling without current injection. A cycle for measuring the noise comprises the same operations as a cycle for measuring the pulmonary impedance, except for the lack of any current injection. It comprises notably the determination of a static impedance due to the noise and a dynamic impedance due to the noise. For each measuring cycle, the digital voltage corresponding to the dynamic impedance due to the noise is compared to a threshold corresponding to an unacceptable level of noise, which is preferably programmable. The threshold can be positive or negative, and there can be a positive threshold and a negative threshold. Each crossing of the threshold causes, for example, the increment of a counter. In a preferred embodiment, the counter is maintained in software or a memory device, and is read and reset to zero periodically by the microprocessor 14. When the counter reaches a predetermined value, the microprocessor 14 decides to suspend the enslavement (i.e., the stimulation frequency is not further determined as a function of the sensed physiological parameter).

The advantages of the invention include the following. First, the same analog circuit elements can be used to realize all steps of sensing the physiological parameter used in the function, and all steps of measuring the noise, which two sets of steps may be offset in time. Stated otherwise, the circuit for measuring the physiological parameter at one time also can be used for sensing noise at a different time. This allows the implementation of noise detection without the need to integrate new circuit components. This saves space and cost, and reduces battery consumption, which are important for implanted medical devices. Further, measuring noise during a sampling of the same type as the sampling during the current injection allows for the detection of parasitic noise even of weak values due to electromagnetic interference.

In addition, the frequency of the cycles for measuring noise can be modified. For example, the frequency can be set to be the same as the frequency of current injection or to another frequency (faster or slower). Similarly, the time between the injection and the sampling of the noise measurement can be constant or can vary. If the measurement of noise takes place at each cycle of injection, and with a delay that is fixed relative to the injection, the beating due to a periodic parasitic signal will be seen in the same manner during the measurement of pulmonary impedance and during the measurement of noise. The parasitic noise perturbing the measure of pulmonary impedance will therefore be well detected.

In one embodiment, the taking of the noise measurement is temporarily halted when the physiological parameter sensor detects a level of patient activity that corresponds to a resting state. For example, when a patient is asleep, the activity level decreases and remains decreased until the patient wakes up. During this time, there is little need to measure noise, and consequently, the measurement can be halted. This has the advantage of reducing the drain on the battery during substantial periods of time when the patient is at rest, and noise is not likely to be a problem with pacing activity. The noise measurement is then resumed when the sensed patient activity level rises above the level corresponding to rest.

In one implementation, the system provides a threshold that is used to control the taking of the noise measurement. The threshold is selected to correspond to a sensed signal representative of an activity level where the patient is no longer at rest. For a description of how such an activity threshold may be set and adjusted over time to provide a threshold suitable for identifying an activity level distinguishing rest from a more active state, reference is made to U.S. Pat. No. 5,303,702, and in particular the discussion therein of the threshold $VE_{LOW}$ and its adjustment. The disclosure of U.S. Pat. No. 5,303,702 is hereby incorporated herein by reference in its entirety.

Another advantage is the fact that the thresholds for comparing the sensed voltage during the measure of noise are programmable. This renders the system flexible, and the criterion of detection is easily modifiable. Similarly, the reading of the counter count by the microprocessor can be set to an adjustable frequency (time interval).

The ability to vary parameters such as the comparison thresholds, the frequency of measurement, the frequency of reading of the number of passings, allows to adapt the sensing system to disruptive noises.

Figure 3:
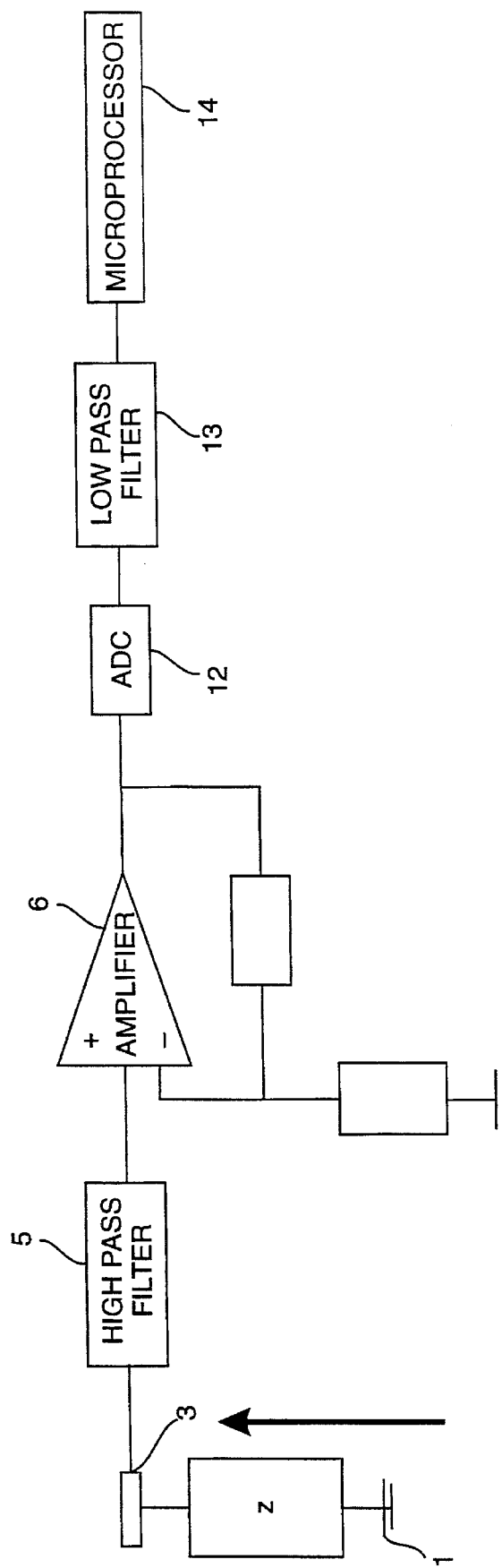
FIG. 3 a schematic diagram of an electronic circuit for measuring the noise according to another embodiment of the invention.

The principle of detection of noise due to electromagnetic interference can be generalized, such that the above-mentioned embodiment represents only one of the possibilities. The voltage obtained at the output of the sensing circuit during the measurement of noise can be processed (for example, by averaging) before the comparison to the threshold is made. The processing circuit of the sensed voltage can be of the type represented on FIG. 3. The voltage amplified by amplifier 6 is digitized by ADC 12, filtered by a filter 13 and the corresponding digital code is read by the microprocessor 14.

The intervention (i.e., the sequence of operation) of the microprocessor can be modified. Thresholds of detection of the noise can be hardwired (fixed) or programmable.

The processing of the voltage obtained at the circuit output and the suspension of the enslavement (function) in case of perturbation can be realized by the microprocessor, by the hardware, or by a combination of the two. The length of the suspension can be determined by the absence of sensed noise for a set time period (which assumes that the system continues to measure the dynamic pulmonary impedance but does not use perturbed signals) or for a set time period.

The example described concerns a rate responsive cardiac pacemaker enslaved (i.e., responsive) to the determined minute ventilation. It should be understood that without departing from the scope of the present invention, the principle can apply equally to other types of enslavements (functional relationships) where the representative magnitude of the sensed physiological parameter (i.e., a useful signal) is susceptible to be perturbed by electromagnetic interferences where the noise perturbations can be sensed separate from the useful signal. Thus, it can be determined when the noise level is too high that the sensed useful signal is deemed too unreliable to use, so that the function of the device during such noise is suspended. It is the case, for example, the enslavement to parameters such as the ejection of blood volume, the temperature, the concentration of a gas (e.g., oxygen saturation) in the blood, the QT interval, etc. which parameters are well known in the art. It should be understood that during the time of suspension of the function, some alternate function that is not susceptible to the noise interference may be provided.

Furthermore, the representative magnitude of the physiological parameter can fulfill other functions than the enslavement of a stimulation frequency, as, for example, the confirmation of the presence of a rhythmic disturbance in an implantable defibrillator or cardioverter.

One skilled in the art will appreciate that the present invention can be practiced by other than the foregoing embodiments, which are presented for purposes of illustration and not of limitation.

We claim:

1. Process of control of an implantable active medical device comprising:

measuring a representative magnitude of a physiological parameter;

providing an enslavement function to enslave the operation of the implantable active medical device to the measured physiological parameter;

measuring a representative magnitude of a noise signal and determining a value of the noise;

comparing the value of the noise to a threshold; and when the value of the noise exceeds the threshold, considering a possible suspension of the enslavement function in response thereto.

2. Process according to claim 1, wherein providing the enslavement function further comprises determining a cardiac stimulation frequency as a function of the measured physiological parameter.

3. Process according to claim 1, wherein the implantable active medical device has a case electrode and a pacemaking function, and measuring the physiological parameter further comprises sensing minute ventilation and measuring the representative magnitude further comprises sensing a voltage between a sensing electrode and the case electrode.

4. Process according to claim 3, wherein sensing the voltage further comprises:

measuring the voltage during an injection of current and determining a dynamic pulmonary impedance therefrom, and measuring the voltage during an absence of a current injection and determining the noise therefrom.

5. Process according to claim 4, further comprising increasing a counter in response to a noise value crossing a noise threshold and suspending the enslavement function in response to the counter reaching a predetermined total.

6. Process according to claim 3, wherein sensing the voltage further comprises measuring the voltage during an injection of current for determining the a dynamic pulmonary impedance and outside of an injection of current for determining the noise value using the same electronic measuring circuit.

7. Process according to claim 6, further comprising:

determining a static pulmonary impedance by integrating preceding measures of dynamic pulmonary impedance; and determining the dynamic pulmonary impedance by taking a difference between the sensed voltage and the static pulmonary impedance.

8. Process according to claim 1 wherein the measuring of the magnitude and determining a value of a noise signal is accomplished only when the measure of the representative magnitude of a physiological parameter exceeds a preselected threshold.

9. An implantable active medical device comprising an electronic circuit for measuring a representative magnitude of a physiological parameter, and a control device to insure an operation of the implantable active medical device as a function of the measured physiological parameter, wherein the electronic circuit further comprises an amplifier having a feedback signal input, an input corresponding to said measured magnitude, and an output, an analog-to-digital converter converting the amplifier output to a digital value, an integrator to integrate the digital values, and a digital-to-analog converter to convert the integrated values to said feedback signal.

10. The device according to claim 9, wherein the physiological parameter is minute ventilation and the control device is operable to produce a cardiac stimulation frequency as a function of the measured minute ventilation.

11. A method of controlling the operation of an implantable active medical device comprising the steps of:

a) sensing a first signal in response to a presence of a useful signal;

b) controlling the operation of the device in a first operating mode as a function of said first signal;

c) sensing a second signal in an absence of the useful signal;

d) determining whether or not the second signal corresponds to noise; and e) considering whether or not to suspend operation in the first operating mode in response to determining that the second signal corresponds to noise.

12. The method of claim 11 wherein steps c) and d) further comprise measuring an amplitude of the second signal, comparing the measured amplitude to a predetermined threshold, and determining that the second signal corresponds to noise when the measured amplitude exceeds the predetermined threshold.

13. The method of claim 12 wherein step d) further comprises adjusting the predetermined threshold to select for an allowable level of noise.

14. The method of claim 12 wherein step e) further comprises counting number of times the measured amplitude exceeds the predetermined threshold, comparing the counted number to a count threshold, and suspending operation in the first operating mode in response to the counted number exceeding the count threshold.

15. The method of claim 14 wherein step e) further comprises counting the number of times the measured amplitude exceeds the predetermined threshold during a preset time interval, comparing the counted number to a count threshold, and suspending operation in the first operating mode in response to the counted number exceeding the count threshold.

16. A method of controlling an operation of an implantable active cardiac control device comprising the steps of:

a) sensing a first signal amplitude corresponding to a presence of a useful signal and representative of a physiological parameter;

b) operating said device in a first operating mode as a function of said sensed first signal amplitude;

c) sensing a second signal amplitude corresponding to an absence of said useful signal and representative of noise;

d) determining whether or not the sensed second signal amplitude corresponds to an unacceptable level of noise; and e) considering whether or not to suspend operation in the first operating mode in response to determining that the second signal corresponds to an unacceptable level of noise.

17. The method of claim 16 wherein step d) further comprises comparing the second signal amplitude to a predetermined threshold, and determining that the second signal amplitude corresponds to an unacceptable level of noise when the sensed second signal amplitude exceeds the predetermined threshold.

18. The method of claim 17 wherein step d) further comprises adjusting the predetermined threshold to select the unacceptable level of noise and operating in the first operating mode until said second signal amplitude exceeds the predetermined threshold.

19. The method of claim 17 wherein step e) further comprises counting a number of times the sensed second signal amplitude exceeds the predetermined threshold, comparing the counted number to a count threshold, and suspending operation in the first operating mode in response to the counted number exceeding the count threshold.

20. The method of claim 19 wherein step e) further comprises comparing the counted number to the count threshold periodically and restarting the counting step at zero thereafter.

21. The method of claim 16 wherein step b) further comprises providing a cardiac stimulation frequency that is a function of the physiological parameter.

22. The method of claim 21 wherein step a) further comprises providing said device with an electronic measuring circuit for sensing the first signal amplitude as a voltage between a sensing electrode and a reference electrode corresponding to minute ventilation.

23. The method of claim 22 wherein:

step a) further comprises measuring said voltage during an injection of current and determining a dynamic pulmonary impedance therefrom; and step c) further comprises measuring said second signal amplitude during an absence of an injection of current for determining noise therefrom.

24. The method of claim 23 wherein step c) further comprises measuring said second signal amplitude as said voltage during the absence of an injection of current using said electronic measuring circuit.

25. The method of claim 23 wherein step d) further comprises comparing the second signal amplitude to a predetermined threshold, and determining that the second signal amplitude corresponds to said unacceptable level of noise when the sensed second signal amplitude exceeds the predetermined threshold.

26. The method of claim 25 wherein step e) further comprises counting a number of times the second signal amplitude exceeds a predetermined threshold, comparing the counted number to a count threshold, and suspending operation in the first operating mode in response to the counted number exceeding the counted threshold.

27. The method of claim 26 wherein step e) further comprises comparing the count number to the count threshold periodically and restarting the counting step at zero thereafter.

28. The method of claim 16 further comprising the step of:
f) determining when the sensed first signal corresponds to a physiological parameter value corresponding to rest activity state, and in response thereto not performing c, d, and e.

29. The method of claim 28 wherein step f) further comprises comparing the sensed first signal to a threshold corresponding to a rest activity level, and determining when the sensed first signal is below said threshold.

30. Apparatus for controlling operation of an implantable active cardiac control device comprising:
a first electronic measuring circuit sensing a first signal amplitude corresponding to a presence of a useful signal and representative of a physiological parameter;
a data processor operating said device in one of a first operating mode performing cardiac control as a function of the sensed first signal amplitude, and a second operating mode performing cardiac control other than as a function of the sensed first signal amplitude;
a second electronic measuring circuit sensing a second signal amplitude during an absence of said useful signal and corresponding to a suspected noise signal; and
means for determining whether or not the sensed second signal corresponds to an unacceptable level of noise;
wherein said data processor further comprises operating means for considering whether or not to suspend operation of said device in the first operating mode in response to determining that the sensed second signal corresponds to an unacceptable level of noise.

31. The apparatus of claim 30 wherein said determining means and operating means further comprise:
a comparator having a first input receiving the first signal amplitude and a second input receiving a predetermined threshold, and an output signal having a first state indicating that the sensed second signal amplitude has exceeded the determined threshold and corresponds to said unacceptable level of noise.

32. The apparatus of claim 31 further comprising means for adjusting the predetermined threshold to select said unacceptable level of noise.

33. The apparatus of claim 31 wherein said operating means further comprises:
a counter to count a number of times the second signal amplitude has exceeded the predetermined threshold;
a second comparator to compare the counted number to a count threshold; and
means for suspending operation in the first operating mode in response to the counter count exceeding the count threshold.

34. The apparatus of claim 33 wherein the data processor further comprises an analog-to-digital converter, a microprocessor, wherein the comparators and counter are implemented in software, and the cardiac control function is a control algorithm relating the sensed first signal to a cardiac control event.

35. The apparatus of claim 33 further comprising means for resetting the counter to zero periodically.

36. The apparatus of claim 30 wherein said data processor first operating mode function further comprises a control algorithm calculating a cardiac stimulation frequency as a function of the sensed first signal representative of a physiological parameter.

37. The apparatus of claim 36 wherein the first electronic circuit further comprises a sensing electrode and a reference electrode, the first sensed signal amplitude is a voltage between the sensing and reference electrodes, and the physiological parameter is a minute ventilation.

38. The apparatus of claim 37 wherein said useful signal is an injection of current and said first electronic circuit determines a dynamic pulmonary impedance from said sensed first signal amplitude; and
said second electronic measuring circuit measures said second signal amplitude during an absence of an injection of current for determining noise therefrom.

39. The apparatus of claim 38 wherein said second electronic measuring circuit is said first electronic measuring circuit and measures said second signal amplitude as said voltage between said sensing and reference electrodes during the absence of an injection of current.

40. The apparatus of claim 38 wherein said operating means further comprises:
a first comparator having a first input receiving the sensed second signal amplitude and a second input receiving a predetermined threshold, and an output signal having a first state indicating that the second signal amplitude has exceeded the predetermined threshold and corresponds to said unacceptable level of noise.

41. The apparatus of claim 40 further comprising means for adjusting the predetermined threshold to select said unacceptable level of noise.

42. The apparatus of claim 40 wherein said operating means further comprises a counter to count a number of times the second signal amplitude has exceeded the predetermined threshold, a second comparator to compare the counter count number to a count threshold, wherein said data processor suspends operation in the first operating mode in response to the counted number exceeding the count threshold.

43. The apparatus of claim 42 wherein the data processor further comprises a microprocessor having said first operating mode and said second operating mode.

44. The apparatus of claim 30 wherein said data processor further comprises second means for determining whether the sensed first signal corresponds to a physiological parameter value corresponding to a rest activity state, wherein said second electronic measuring circuit and determining means are responsive to said second determining means for not sensing said second signal in response to the sensed first signal corresponding to a rest activity state.

45. The apparatus of claim 44 wherein said second determining means further comprises a comparator having the sensed first signal as an input and an activity threshold as an input, a first output corresponding to an activity state when the first signal is above the threshold and a second output corresponding to a rest state when the first signal is below the threshold, the second electronic measuring circuit being responsive to said second output.

* * * * *

UNITED STATES PATENT AND TRADEMARK OFFICE
CERTIFICATE OF CORRECTION

PATENT NO. : 5,522,860
DATED : June 4, 1996
INVENTOR(S) : Renzo D. Molin, et. al.

It is certified that error appears in the above-indentified patent and that said Letters Patent is hereby corrected as shown below:

Column 7, line 7, after "determining" delete "the";

Column 7, line 63, after "counting" insert --a--;

Column 9, line 17, after "corresponding to" insert --a--;

Column 9, line 18, after "performing" insert -- steps--

Signed and Sealed this

Twenty-sixth Day of August, 1997

*Attest:*

BRUCE LEHMAN

*Attesting Officer*  *Commissioner of Patents and Trademarks*